United States Patent
Keramidas et al.

(10) Patent No.: US 6,716,873 B1
(45) Date of Patent: Apr. 6, 2004

(54) TOCOPHEROL ESTER COMPOUNDS

(75) Inventors: Anastasios Keramidas, Nicosia (CY); Andreani Odysseos, Nicosia (CY); Andreas Michael Papas, Kingsport, TN (US)

(73) Assignee: Yasoo Health Inc., Johnson City, TN (US)

( * ) Notice: Subject to any disclaimer, the term of this patent is extended or adjusted under 35 U.S.C. 154(b) by 0 days.

(21) Appl. No.: 10/392,225

(22) Filed: Mar. 20, 2003

(51) Int. Cl.$^7$ .................... A61K 31/355; C07D 311/72
(52) U.S. Cl. .................... 514/458; 549/407; 549/410
(58) Field of Search ................. 549/410, 407; 514/458

(56) References Cited

U.S. PATENT DOCUMENTS 4,039,559 A * 8/1977 Nakamura .................. 549/410
6,387,882 B1 * 5/2002 Ogata et al. ................. 514/18
6,645,998 B2 * 11/2003 Sanders et al. ............. 514/456

* cited by examiner

Primary Examiner—D. Margaret Seaman
Assistant Examiner—Raymond Covington

(57) ABSTRACT

Disclosed are novel tocopherol ester compounds having the formula (I)

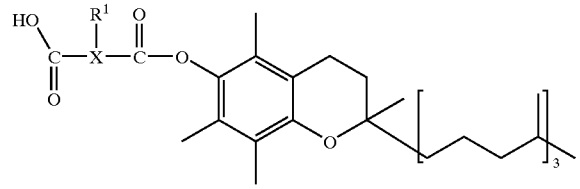

wherein X is a chain of 2 or 3 carbon atoms, e.g., ethylene and trimethylene, joining the 2 carbonyl groups to which they are bonded; and $R^1$ is a group having the formula —Y—$R^4$ wherein Y is a selenium, tellurium or sulfur atom and $R^4$ is an alkyl, cycloalkyl or aryl radical. The tocopherol ester compounds of formula (I) exhibit antiproliferative and growth inhibitory effects on breast cancer cell lines.

15 Claims, No Drawings

TOCOPHEROL ESTER COMPOUNDS

FIELD OF THE INVENTION

This invention pertains to certain novel tocopherol ester derivatives and intermediate compounds utilized in the preparation of the derivatives. More specifically, this invention pertains to α-tocopherol ester compounds that exhibit antiproliferative and growth inhibitory effects on breast cancer cell lines and to substututed dicarboxylic acids and anhydrides.

BACKGROUND OF THE INVENTION

Selenium and α-tocopherol (Vitamin E) are two antioxidants that have attracted great attention due to their cancer chemo-preventive activity showing strong synergism. See, for example, Ip, *J. Nutr.* 128, 1845–1854 (1998); Clark, et al., *J. Am. Med. Assoc.* 276, 1957–1963 (1996); El-Bayoumy, *Mutation Research* 475, 123–139 (2001); Alaejos, et al., *Nutrition* 16, 376–383 (2000); Burton, et al., *Arch. Biochem. Biophys.* 221, 281–290 (1983), and Burton, et al., *Acc. Chem. Res.* 19,194–201. Thus, the impact of selenium deficiency on cancer risk seemed to be more profound at low serum vitamin E concentrations as reported by Salonen, et al., *Br. Med. J.* 290, 417–420 (1985), Willett, et al., *Lancet* July 16; 2(8342):130–134 (1983), and Shamberger, et al, *Arch. Environ Health* 31, 231–235 (1976).

The reported synergism may be attributed to the redox recycling of the antioxidants [Chaudiere, et al., *Food Chem. Toxicology* 37, 949–962 (1999) and Ip, *Federation Proc.* 44, 2573–2578 (1985)] although d-α-tocopherol is suggested to develop an environment of decreased oxidative stress where the anticarcinogenic action of selenium is potentiated through specific molecular mechanisms. Other mechanisms by which selenium compounds spare α-tocopherol in the cells also have been suggested by Li, et al., *FEBS Letters* 508, 489–492 (2001). Previous studies on the cell growth inhibitory effects of vitamin E compounds and derivatives have shown that RRR-α-tocopheryl succinate (VES) has the most potent apoptotic effect in vitro [13. Yu, et al., *Nutr. Cancer* 33, 26–32 (1999)]. As reported by Cheeseman, et al., *Free Radic Biol Med.* 19, 591–598 (1995) and Papas, Tocopherols and Tocotrienols, in A. M. Papas (Ed.) Antioxidant Status, Diet, and Health, pp. CRC Press, Boca Raton, USA, (1998), the succinate derivative of tocopherol is used extensively as a food additive or nutritional supplement because it is more stable than free tocopherol and equally bioavailable in healthy humans. Although the formation of the ester bond blocks the 6-hydroxyl group of the d-α-tocopherol and inhibits the antioxidant activity, VES can be hydrolyzed retaining the active free d-α-tocopherol antioxidant activity.

According to Yu, et al., *Nutr. Cancer* 33, 26–32, this pro-apoptotic effect of VES has not been shared by pure d-α-tocopherol, an effect that can be attributed to the structural modification of the molecule of tocopherol by the succinic esteric bond. This is suggested to enable the esterified form to interact with specific molecules in the biologic process of signal generation and transduction [Yu, et al., *Nutr. Cancer* 27, 267–278 (1997) and Turley, et al., *Cancer Res.* 57, 881–890 (1997)]. It appears from the accumulated evidence [Jiang, et al., *Bioch. Biophys. Res. Commun.* 194, 836–841 (1993); Kaeck, et al., *Biochem. Pharmacol.* 53, 921–926 (1997); Lu, et al., *Carcinogenesis* 17, 1903–1907 (1996); Lu, et al., *Biochem. Pharmacol.* 49, 1531–1535 (1994); Lu, et al., *Biochem. Pharmacol.* 50, 213–219 (1995); and Wilson, et al., *Biochem. Pharmacol.* 43, 1137–1141 (1992)] that the chemical form of selenium is a very important factor in eliciting defined cellular responses in the in vitro system. Aromatic selenium compounds have been preferred to other types of organic selenium compounds due to their higher stability and lower toxicity [Ip, *J. Nutr.* 128, 1845–1854 (1998); Ganther, et al., *Tetrahedron* 53, 12299–12310 (1997); and Ganther, et al., *Bioorg. Med. Chem.* 9,1459–1466 (2000). Specific molecular mechanisms of their preventive action remain to be elucidated.

BRIEF SUMMARY OF THE INVENTION

We have discovered that certain derivatives of α-tocopherol exhibit cell growth inhibitory properties such as antiproliferative and growth inhibitory effect on breast cancer cell lines. Thus, the present invention provides α-tocopherol ester compounds having formula (I):

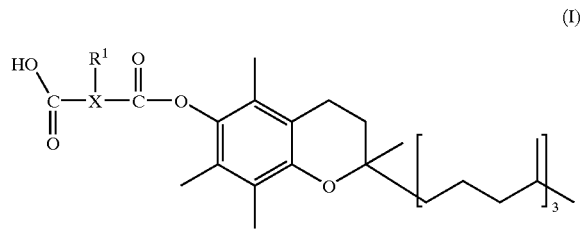

(I)

wherein X is a chain of 2 or 3 carbon atoms, e.g., ethylene and trimethylene, joining the 2 carbonyl groups to which they are bonded; and $R^1$ is a group having the formula —Y—$R^4$ wherein Y is a selenium, tellurium or sulfur atom and $R^4$ is an alkyl cycloalkyl or aryl radical. Certain of the compounds of formula (I) have shown significant antiproliferative and growth inhibitory effect on breast cancer cell lines.

Another embodiment of the present invention is a process for the preparation of compounds of formula (I) by the steps comprising:

(1) contacting a compound having the formula Z—Y—$R^4$ with a dicarboxylic acid anhydride having the formula:

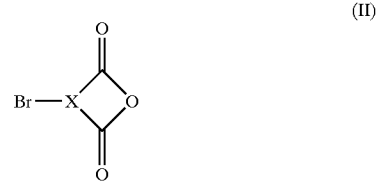

(II)

in the presence of an alkanol having the formula $R^3$—OH to obtain an ester having the formula:

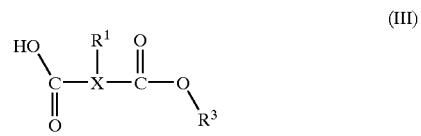

(III)

(2) separating the ester of formula (III) produced in step (1) from the alkanol solvent;

(3) contacting the ester of formula (III) with aqueous inorganic acid to convert the ester to the corresponding dicarboxylic acid;

(4) contacting the dicarboxylic acid formed in step (3) with acetic anhydride to convert the dicarboxylic acid to an anhydride having the formula:

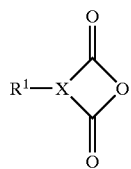

(IV)

and (5) contacting the anhydride of formula (IV) with RRR-α-tocopherol to obtain an α-tocopherol ester having formula (I);

wherein X and $R^1$ are defined above; $R^3$ is alkyl of 1 to 3 carbon atoms and Z is an alkali metal.

The compounds having the formula (V) are especially preferred:

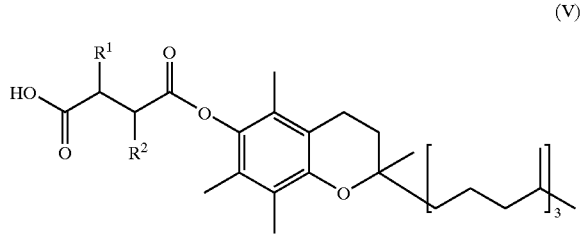

(V)

wherein $R^1$ and $R^2$ each is hydrogen or phenylselenyl, i.e., phenyl-Se-, provided that $R^1 \neq R^2$, i.e., one of $R^1$ and $R^2$ is phenylselanyl and the other is hydrogen. The compounds of formula (V) exhibit antiproliferative and growth inhibitory effects on breast cancer cell lines superior to the effect of α-tocopheryl succinate and its equimolar combination with 2-phenylselanyl-succinic acid.

DETAILED DESCRIPTION

The compounds of our invention may be prepared by means of known procedures using available materials. For example, the compounds may be prepared by contacting RRR-α-tocopherol with an anhydride having formula (IV) in the presence of an acidic catalyst and a hydrocarbon solvent. For example, phenylselenosuccinic anhydride may be contacted with α-tocopherol in the presence of zinc chloride and toluene. The compounds of formula (I) typically comprise a mixture of compounds, e.g., phenylselanyl-succinic acid RRR-α-tocopherol having the structure

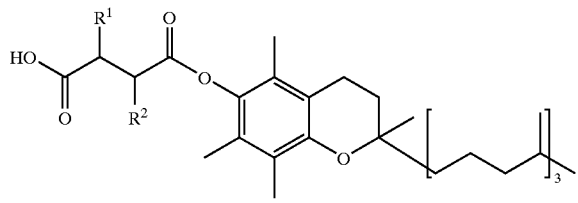

typically comprises a mixture of the 2-phenylselanyl compound [Compound (I)—$R^1$=H, $R^2$=phenylselanyl] and the 4-phenylselanyl compound [Compound (I)—$R^1$= phenylselanyl, $R^2$=H]. The anhydride having formula (IV) may be obtained by contacting the corresponding dicarboxylic acid with acetic anhydride at elevated temperatures. The dicarboxylic acid is obtained by the hydrolysis of an ester of formula (III) at elevated temperature using a mineral acid such as hydrochloric acid. Ester (III) X can be prepared by first contacting a compound having the formula $R^4$—Y—$R^4$, e.g., diphenyldiselenide, with an alkali metal borohydride, e.g., sodium borohydride in the presence of an alkanol solvent, e.g., methanol, and then adding bromosuccinic anhydride to the alkanol soluton of the Z—Y—$R^4$ intermediate. Anhydride (II) can be obtained by heating bromosuccinic acid with acetic anhydride.

The groups represented by $R^4$ may be unsubstituted or substituted alkyl, cycloalkyl or aryl containing up to about 20 carbon atoms. The alkyl radicals preferably are alkyl of 1 to about 6 carbon atoms. Examples of the aryl groups include phenyl and phenyl substituted with one or two substituents selected from alkyl, alkoxy, nitro, halogen and the like. $R^1$ most preferably represents a phenylselenyl group.

EXAMPLES

The preparation and utility of the compounds of the present invention is further illustrated by the following experiments and procedures. NMR (Nuclear Magnetic Resonance) spectra were recorded on a Bruker Avance 300 spectrometer operating at 300 MHz for $^1$H and 75 MHz for $^{13}$C. The $^1$H and $^{13}$C NMR spectra were recorded using a sweep width of 6000 and 19000 Hz respectively and pulse angle 30°. The 2D $^1$H NMR COSY-45 experiments (pulse sequence (90°-$t_1$-45°) were conducted using 256 increments (each consisting of 16 scans) covering the full spectrum (12.0 ppm in both dimensions). The standard NOESY pulse sequence (90°-$t_1$-90°-tm-90°) was used in the 2D $^1$H EXSY-NOESY measurements and these spectra were acquired 512 increments (with 16 scans each) covering full spectra (12.0 ppm in both dimensions) and 0.25 s mixing time. 2D $^{13}$C, $^1$H HETCOR experiments were conducted using 256 increments (each consisting of 32 scans) covering full spectra (12.0 ppm on F1 and 120 ppm on F2 dimensions). The phase sensitive HMQC sequence enriched with BIRD filter and GARP decoupling (90°) was applied at inverse H, C correlation for the 2D HMQC spectra.

Example 1

Bromosuccinic acid (5.00 g, 25.4 mmol) and excess acetic anhydrite (5.18 g, 50.7 mmol) were mixed and refluxed for 2 hours. The solvent was evaporated under vacuum to give a viscous brown liquid. The isolated yield of bromosuccinic anhydride was 4.54 g (100%). $^1$H NMR δ(CDCl$_3$) (ppm): 4.89 (dd, 1H, $C^{2"}(H_x)$Br), 3.74 (dd, 1H, $C^{3"}(H_A)(H_B)$), 3.27 (dd, 1H, $C^{3"}(H_A)(H_B)$). $^{13}$C{$^1$H} NMR δ(CDCl$_3$) (ppm): 168.67 ($C^{1"}$), 168.02 ($C^{4"}$), 40.06 ($C^{2"}$), 33.94 ($C^{3"}$).

NaBH$_4$ (0.2 g, 5 mmol) was slowly added within 30 minutes to a methanol (10 mL) solution of diphenyldiselenide (0.44 g, 1.4 mmol) at 0° C. under nitrogen atmosphere. The yellow solution became colorless and the mixture was stirred for an additional hour at 0° C. A deoxygenated solution of bromosuccinic anhydride (0.50 g, 2.9 mmol) in methanol (5 mL) was added to the mixture. Within five minutes, a white solid precipitated and stirring was continued for another two hours at room temperature. Methanol was evaporated under vacuum and n-hexane (10 mL) was added to the resulting yellow solid. The 2-phenylselanyl-succinic acid 4-methyl ester product was extracted with H$_2$O (3×10 mL) and the aqueous phase was acidified with HCl 6N, forming a yellow oil, which was extracted with CH$_2$Cl$_2$ (3×10 mL). The organic phase was dried with $Na_2SO_4$ and the solvent was evaporated under vacuum to provide 0.71 g (87%) of yellow oil. The primary product obtained was 2-phenyl-selanylsuccinic acid 4-methyl ester with a minor amount, e.g., less than 5%, of the isomeric 2-phenylselanyl-succinic acid-1-methyl ester. $^1$H NMR δ($CDCl_3$) (ppm): 10.6 (br, 1H, $C^{1"}$(O)OH), 7.59 (m, 2H, $C^{6"}$H, $C^{10"}$H), 7.35 (m, 3H, $C^{7"}$H, $C^{8"}$H, $C^{9"}$H), 3.97 (dd, 1H, $H_xC^{2"}$), 3.67(s, 3H, $H_3CO(O)C^{4"}$-), 3.04 (dd, 1H, $C^{3"}H_AH_B$), 2.81(dd, 1H, $C^3 \square H_AH_B$). $^{13}$C{$^1$H} NMR δ($CDCl_3$) (ppm): 178.40 ($C^{1"}$), 171.50 ($C^{4"}$), 136.62 (C6", $C^{10"}$), 129.69 ($C^{7"}$, $C^{8"}$, $C^{9"}$), 126.79 ($C^{5"}$), 52.54 ($H_3$CO(O)$C^{4"}$), 37.21 ($C^{2"}$), 36.95 ($C^{3"}$). $^{77}$Se NMR δ($CDCl_3$) (ppm): 646.95 (d).

HCl 12N (10 mL) was added to the 2-phenylselanyl-succinic acid methyl ester (0.70 g, 2.4 mmol) prepared as described above and the mixture was refluxed overnight at 75° C. The resulting solution was cooled at room temperature and a white solid precipitated. The solid was collected by filtration, washed with $CH_2Cl_2$ (2×3mL) and dried under vacuum. The isolated yield of phenylselanyl-succinic acid (PSSA) was 0.55 g (82%). Found: C, 43.23; H, 3.92. $C_{10}H_{10}O_4Se \cdot 0.25H_2O$ requires C, 43.26; H 3.81%. $^1$H NMR δ($CD_3CN$) (ppm): 7.65 (d, 2H, $C^{6"}$H, $C^{10"}$H), 7.40 (m, 3H, $C^{7"}$H, $C^{8"}$H, $C^{9"}$H), 3.90 (dd, 1H, $C^{2"}H_x$), 2.78 (m, 2H, $C^{3"}H_2$). $^{13}$C{$^1$H} NMR δ($CD_3CN$) (ppm): 173.2 ($C^{1"}$), 172.2 ($C^{4"}$), 136.2 ($C^{6"}$, $C^{10"}$), 130.0 ($C^{7"}$,$C^{9"}$), 129.4 (C8"), 127.2 (C5"), 37.0 (C2"), 36.6 ($C^{3"}$). $^{77}$Se NMR δ($CD_3CN$) (ppm): 634.8 (d).

Phenylselanyl-succinic acid (0.55 g, 2.0 mmol) and excess acetic anhydrite (10 mL) were stirred at 30° C. for 2 hours. Acetic anhydride was evaporated under vacuum to provide 0.51 g (100%) of phenylselanyl-succinic anhydride as a gray solid. $^1$H NMR δ($CD_3CN$) (ppm): 7.64 ($C^{6"}$H, $C^{10"}$H), 7.40 ($C^{7"}$H, $C^{8"}$H, $C^{9"}$H), 3.91 (dd, $C^{2"}H_x$), 2.79 (m, $C^{3"}H_2$). $^{13}$C NMR δ($CD_3CN$) (ppm): 173.2 ($C^{1"}$), 172.3 ($C^{4"}$), 136.2 ($C^{6"}$, $C^{10"}$), 129.6 ($C^{7"}$, $C^{9"}$), 129.4 $C^{8"}$), 127.2 ($C^{5"}$) 37.0 ($C^{2"}$), 36.6 ($C^{3"}$). 77Se NMR δ($CD_3CN$) (ppm): 634.8 (d).

To a toluene (20 mL) solution of RRR-α-tocopherol (0.30 g, 0.70 mmol) were added phenylselanyl-succinic anhydride (0.58 g, 2.3 mmol) and $ZnCl_2$ powder (0.17 g, 1.3 mmol) dried with $SOCl_2$. The resulting mixture was stirred and refluxed under $N_2$ for one day. Then the mixture was filtered and the solvent was removed under vacuum. The oily residue was redissolved in 1–2 mL $CHCl_3$ and was passed through a well-packed chromatography column (2 cm×25 cm) using as eluents first n-hexane then a chloroform/n-hexane mixture, chloroform and finally ethyl acetate. The major quantity of 2-phenylselanyl-succinic acid RRR-α-tocopherol ester (PSSA-α-Toc) passes though the column with the chloroform/hexane mixture. The solvent was evaporated under vacuum yielding 0.27 g (55%) of a brownish oil containing 70% of 2-phenylselanyl-succinic acid-1-RRR-α-tocopherol ester (PSSA-1-α-Toc) and 30% of 2-phenylselanyl-succinic acid-4-RRR-α-tocopherol ester (PSSA-4-α-Toc). TLC (hexane:$CHCl_3$, 1:5) $R_{α-tocopherol}$=0.69, $R_{PSSA-α-Toc}$=0.11. Found: C, 68.91; H, 8.84. $C_{39}H_{58}O_5Se \cdot 0.3$n-hexane requires C, 68.86; H, 8.81%. $^1$H NMR $\square$($CDCl_3$) (ppm): (PSSA-1-α-Toc) 11.1 (br, 1H, HO(O)$C^{4"}$), 7.71 (d, 2H, $C^{6"}$H, $C^{10"}$H), 7.36 (m, 3H, $C^{7"}$H, $C^{8"}$H, $C^{9"}$H), 4.02 (dd, 1H, $C^{2"}H_x$), 3.12 (dd, 1H, $C^{3"}$ $(H_A)(H_B)$), 3.02 (dd, 1H, $C^{3"}$ $(H_A)(H_B)$), 2.47 (m, 2H, $C^4H_2$), 1.99 (s, 3H, $C^{12}H_3$), 1.90 (s, 3H, $C^{13}H_3$), 1.86 (s, 3H $C^{14}H_3$), 1.70 (m, 2H, $C^3H_2$), 1.38 (m, 3H, $C^{4"}$H, $C^{8"}$H, $C^{12"}$H), 1.16 (s, 3H, $C^{11"}H_3$), 1.35–0.9 (m, 18H, $CH_2$-phytyl), 0.78(t, 12H, $H_3$C-phytyl); (pssa-4-α-toc) 11.1 (br, 1H, HO(O)$C^{1"}$), 7.71 (d, 2H, $C^{6"}$H, $C^{10"}$H), 7.36 (m, 3H, $C^{7"}$H, $C^{8"}$H, $C^{9"}$H), 4.15 (dd, 1H, $C^{2"}H_x$, 3.05 (dd, 1H, $C^{3"}(H_A)(H_B)$), 2.85 (dd, 1H, C3" $(H_A)(H_B)$), 2.47 (m, 2H, $C^4H_2$), 2.01 (s, 3H, $C^{12}H_3$), 1.90 (s, 3H, $C^{13}H_3$), 1.86 (s, 3H, $C^{14}H_3$), 1.70 (m, 2H, $C^3H_2$), 1.38 (m, 3H, $C^{4"}$H, $C^{8"}$H, $C^{12"}$H), 1.16 (s, 3H, $C^{11"}H_3$), 1.35–0.9 (m, 18H, —$CH_2$-phytyl), 0.78(t, 15H, $H_3$C-phytyl). $^{13}$C{$^1$H} NMR δ($CDCl_3$) (ppm): (pssa-1-α-toc) 177.93 ($C^{4"}$), 170.16 ($C^{1"}$), 149.93 ($C^9$, 140.75 ($C^6$), 136.66 ($C^6\square$,$C^{10"}$), 129.78 ($C^{7"}$, $C^{9"}$), 129.40 ($C^{8"}$), 127.65 ($C^7$), 127.03 ($C^5$), 125.33 ($C^{5"}$), 123.50 ($C^{10}$), 117.87 ($C^8$), 75.48 ($C^2$), (39.81, 37.81, 37.72, 33.19, 33.11, 25.22, 21.45) (C'$H_2$), 36.89 ($C^{3"}$), 37.12 ($C^{2"}$), 31.46 ($C^3$), 28.39 ($C^{4"}$,$C^{8"}$,$C^{12"}$), 24.86 ($C^{11}$), (23.14, 23.05) ($H_3CC^{4"}$,$H_3CC^{8"}$), 20.98 ($C^4$), (20.10) (($H_3C)_2C^{12"}$), 13.37 ($H_3CC^{14}$), 12.53 ($H_3C$ $C^{13}$), 12.22 ($H_3CC^{12}$); (pssa-4-α-toc) 176.93 ($C^{1"}$), 171.53 ($C^{4"}$), 149.93($C^9$), 140.67 ($C^6$), 135.98 ($C^{6"}$,$C^{10"}$), 129.70 ($C^{7"}$, $C^{9"}$), 129.40 ($C^{8"}$), 127.38 ($C^7$), 126.86 ($C^5$), 125.93 ($C^{5"}$), 123.50 ($C^{10}$), 117.87 ($C^8$), 75.48 ($C^2$), (39.81, 37.81, 37.72, 33.19, 33.11, 25.12, 21.45) (C'$H_2$), 37.52 (C3"), 36.27 ($C^{2"}$), 31.46 ($C^3$), 28.39 ($C^{4"}$,$C^{8"}$, $C^{12"}$), 24.86 ($C^{11}$), (23.14, 23.05) ($H_3CC^{4"}$,$H_3CC^{8"}$), 20.98 ($C^4$), (20.10) (($H_3C)_2C^{12"}$), 13.37 ($H_3CC^{14}$), 12.53 ($H_3CC^{13}$), 12.22 ($H_3CC^{12}$). $^{77}$Se NMR α($CDCl_3$) (ppm): (PSSA-1-α-Toc) 652.1(d), (PSSA4-α-Toc) 635.7(d).

The reaction of RRR-α-tocopherol with phenylselanyl-succinic anhydride produces a PSSA-α-Toc product consisting of two isomers: the PSSA-1-α-Toc and the PSSA4-α-Toc in 7 to 3 ratio, respectively, as evidenced by $^{77}$Se and $^1$H NMR spectra. Complete assignment of the peaks observed in the NMR spectra was done by analyzing the chemical shifts, the integrals and the 2D $^1$H-COSY, $^1$H-NOESY, $^{13}$C, $^1$H-HETCOR and $^1$H, $^{13}$C-HMQC spectra. The $^{77}$Se chemical shifts are very sensitive to the chemical environment of the selenium atom and gave valuable structural information as for example in the identification of the PSSA-Me and PSSA-α-Toc isomers. The peak of the selenium nucleus was affected from the esterification of the nearest carboxylic group [-$C^{2"}$(SePh)(H)$C^{1"}$(O)OR] in PSSA that cause a shift towards lower field (635 ppm in PSSA and 636 ppm in PSSA4-α-Toc compared to 652 ppm in PSSA-1-α-Toc). The $^{13}$C NMR spectrum of PSSA in $CD_3CN$ reveals some interesting features. The $C^{1"}$ carboxylic atom resonance is affected by the selenium substituent on $C^{2"}$ and is shifted at higher field (176.93 ppm) compared to $C^{4"}$ (177.93 ppm). This is in agreement with the chemical shifts observed for other selenium containing organic acids: Doudin, et al., *J. Chem. Soc. Perkin Trans.* 1723–729. Similar order observed for the chemical shifts of the carboxylate esters {170.56 ppm for $C^{1"}$ in PSSA-1-α-Toc [-$C^{2"}$(SePh)(H)$C^1\square$(O)O-α-Toc] compare to 171.53 ppm for $C^{4"}$ in PSSA4-α-Toc [-$C^{2"}$(SePh)(H)$C^3\square H_2C^4\square$(O)O-α-Toc]}.

The selenium compounds of formula (I) are stable in the solid state and in organic solvent solutions for several months. However, addition of base causes decomposition of the compounds and formation of phenylselenol salt and unsaturated carboxylic acids. The reaction is slow at room temperature (less than 5% of an aqueous solution of PSSA at pH=9 decomposed in one day as evidenced by $^1$H NMR) and accelerates at higher temperature. In the culture media both PSSA and PSSA-α-Toc are stable for more than one weak as evidenced by TLC.

The mixture of the two isomers of PSSA4-α-Toc and PSSA-1-α-Toc in 3:7 ratio was used in cell viability assays with WST-8 and crystal violet on the estrogen-receptor positive MCF-7 and the estrogen-receptor negative MDA-MB-231 cancer cell lines. Breast cancer cell lines were selected due to the previous reports suggesting specific molecular apoptotic mechanisms triggered by VES through Fas and TGF-beta [Yu, et al., *Nutr. Cancer,* 27, 267–278; Turley, et al., *Cancer Res.,* 57, 881–890]. The activation of these pathways has not been shared by pure d-α-tocopherol and, therefore, is attributed to the structural modifications of this molecule within the succinate ester.

Cultures of MDA-MB-231 cells were maintained at 37° C. in minimum essential medium containing 3.7 g of $NaHCO_3$ per liter of water, supplemented with 10% (v/v) Fetal Bovine Serum and 1% Penicillin/Streptomycin (broad spectrum antibiotics). MCF-7 cell line was maintained in minimum essential medium containing 3.7 g $NaHCO_3$ supplemented with 10% Fetal Bovine Serum, 1 mmol/L sodium pyruvate, 10 μg/mL insulin and 1% (v/v) fungisone (antibiotic/antimycotic). The media were equilibrated with a humidified atmosphere of 5% $CO_2$. Stock cultures were seeded at a density of $200 \times 10^3$ cells/mL and allowed to multiply to confluence. The cells were grown at 37° C. in a humidified atmosphere containing 5% $CO_2$ and passaged when confluent using 0.25% trypsin.

Experimental media. Stock solutions of RRR-α-tocopheryl succinate (VES, 10.00 mg), phenylselanyl-succinic acid (PSSA, 5.15 mg), and PSSA-α-Toc (13.24 mg) in pure ethanol (1 mL) were diluted into the culture medium so that the final concentration of ethanol was 0.1%. The same amount of ethanol was added to the control samples. Stock solutions were maintained at 4° C.

Cell viability assays. The first method employs a novel tetrazolium salt, WST-8 [2-methoxy-4-nitrophenyl)-3(4-nitrophenyl)-5-(2,4-disulphophenyl)-2-H-tetrazolium, monosodium salt] which produces a highly water-soluble formazan dye generated by dehydrogenases which are active in living cells in a culture medium. For initial growth assays, cell suspensions (5000 cells/100 μL/well) were dispensed onto 96-well microtiter plates and incubated at 37° C., 5% $CO_2$ for 1–12 days. At distinct time intervals 10 μL of the WST-8 solution was added to each well and allowed to incubate for 2–4 hrs. A yellow formazan dye is developed only in living cells. The absorbance, subsequently measured using a microplate reader (EMS Reader with dispenser, Genesys Software), is directly proportional to the number of living cells and, therefore, indirectly proportional to the cell growth inhibitory capacity of the compound used. The absorbance at 450 nm was measured using a microplate reader (EMS Reader with dispenser, Genesys Software) with a reference wavelength at 600 nm. The second method employs an aqueous solution containing 0.2% crystal violet and 2% ethanol (90.2 g CV in 100 mL water plus 2 mL of ethanol). Cell viability is determined by staining cells with the crystal violet solution and assessing the OD620 of the cell lysates, which correlates to cell number. For both methods, cell suspensions (5000 cells/100 μ☐L culture media) were initially inoculated on a 96-well microplate and preincubated in an incubator for 48 hrs to allow attachment 10 μL of the stock solution of each compound was added so that the final concentration was equimolar for each compound corresponding to 10 ☐g/mL of VES. Treatments were performed in triplicate points (three measurements each) and results are given as the mean values of three experiments+/−SD.

Statistical analysis. Comparison of the effect of the different compounds on absorbance at the appropriate wavelength was made by analysis of variance (ANOVA). Post-hoc comparisons were made with Dennet's t-test which treats one group as control and compares the others against it.

Example 2

The effects of equimolar concentrations of sodium selenate, PSSA and PSSA-α-Toc on the viability of MCF-7 cells were compared using the procedures described above. Cells were plated in triplicate in 96-well plates and allowed to attaach and reach confluence for 48 hours. On Day 2 test compounds were added at equimolar concentrations corresponding to 10 μg/mL of VES. Cell viability was determined at the specified times by staining with crystal violet and measuring the OD620 of the cell lysates. The results, representing the mean of triplicate points+/−SD, are shown in Table I.

TABLE I

| Day | Control | PSSA | PSSA-α-Toc | Na Selenate |
|---|---|---|---|---|
| 0 | 0 | 0 | 0 | 0 |
| 2 | 0.346926 | 0.384248 | 0.324973 | 0.073438 |
| 5 | 1.275266 | 1.217939 | 0.950412 | 0.061167 |
| 7 | 1.681166 | 1.693292 | 1.227321 | 0.082 |
| 9 | 1.371392 | 1.495334 | 1.162440 | 0.054111 |

Example 3

Inhibition of growth of MCF-7 cells after incubation with equimolar concentrations of VES, PSSA, 1:1 by weight mixture of VES with PSSA, and PSSA-α-Toc was determined using the procedures described above. Cells were plated in triplicate in 96-well plates and incubated for 48 hours to allow attachment. Equimolar concentrations of the different compounds were added on day 2 and allowed for incubation for the indicated time period. At the specified time 10 μL of the tetraszolium salt WST-8 was added to each well, the cells were allowed to incubate for 4 hours and optical density (OD) measurements of the yellow formazan dye were made at 450 nm. The results are shown in Table II wherein the values given are the average of mean values from three experiments ±SD and Mixture refers to a 1:1 by weight mixture of VES with PSSA.

TABLE II

| Day | Control | VES | PSSA | Mixture | PSAA-α-Toc |
|---|---|---|---|---|---|
| 0 | 0 | 0 | 0 | 0 | 0 |
| 2 | 0.87225 | 0.8005 | 0.914857 | 0.78725 | 0.780625 |
| 4 | 1.6142 | 1.439 | 2.018667 | 1.654714 | 1.4215 |
| 7 | 3.414333 | 3.311444 | 3.617778 | 3.372444 | 2.998 |
| 9 | 3.560222 | 3.427333 | 3.54125 | 3.4334 | 2.812 |
| 11 | 3.3862 | 2.989833 | 3.451143 | 2.9225 | 2.105222 |

Example 4

Comparison of the inhibitory effects of 5-fluorouracil (5-FU, 300 nM), VES (10 μg/mL), PSSA (5.15 μg/mL), 1:1 equimolar combination of VES with PSSA (10 μg/mL+5.15 μg/mL) and PSSA-α-toc (13.24 μ☐g/mL) on MDA-MB-231 cell growth. Cells were seeded in triplicate in 96-well plates and incubated for 48 hrs to allow attachment. The different compounds were added at the indicated concentrations and allowed to incubate for an additional 4 days. The indicated incubation time previously was determined in a growth assay ats the time of maximal proliferation rate. Tetrazolium salt WST-8 (10 μL) was added to each well, the cells were allowed to incubate for 2 hours and optical density (OD) measurements of the yellow formazan dye were made at 450 nm. The absorbance values for each of the three experiments+/−SD after six days of incubation are shown in Table III.

TABLE III

| Control | 5-FU | VES | PSSA | Mixture | PSSA-α-Toc |
|---------|------|-----|------|---------|-----------|
| 0.423 | 0.415 | 0.340 | 0.411 | 0.310 | 0.208 |
| 0.414 | 0.411 | 0.335 | 0.412 | 0.295 | 0.205 |
| 0.432 | 0.413 | 0.341 | 0.412 | 0.325 | 0.203 |

A cell growth inhibitory effect, rather than a cytotoxic effect, initially was determined for PSSA-α-Toc in a cell viability assay where equimolar concentrations of sodium selenate, PSSA and PSSA-α-Toc were compared (FIG. 1). Sodium selenate at 3.26 µg/mL (equimolar to 10 µg/mL of VES) had a 100% cytotoxic effect on MCF-7 cells. The mixture of pssa had no measurable effect compared to control whereas a marginal increase in absorbance could be observed with prolonged incubation. Interestingly, PSSA-α-Toc inhibited cell growth much more effectively. Day 7 post-treatment has been determined as the day of maximal proliferation rate. PSSA-α-Toc and sodium selenate show statistically significant decrease in cell growth. FIG. 2 shows the effect on cell viability of MCF-7 after 10 days of incubation with equimolar concentrations of VES, pssa, VES in 1:1 combination with pssa and pssa-□-toc. PSSA had no inhibitory effect over the first 7 days of incubation and this effect became only marginal with longer incubation. VES inhibited cell growth more effectively during the first 7 days of incubation, which correlate with the exponential phase of the growth curve (data not shown). The further decrease in absorbance rate with longer incubation is only attributed to the already significant reduction of the viable cell number. Their 1:1 combination was not more effective than VES alone, suggesting that the two compounds have no biochemical interactions modifying their cell growth inhibitory properties in the culture media. PSSA-α-toc had the most potent inhibitory effect throughout the culture period. This is also shown by the post-hoc analysis of the data, which yields significant differences between PSSA-α-Toc and the other compounds. This effect can be attributed to the activation of a specific cell growth inhibitory pathway. Whether this pathway is associated to the ones triggered by VES alone, or is unique to the structural modifications of both VES and pssa in this novel compound is currently under investigation. As can be seen in FIG. 2, most cells were viable at concentration equivalent to $IC_{50}$ (data from dose-response curve which are not shown), suggesting that the PSSA-α-Toc is not cytotoxic but it rather exerts an antiproliferative and cell growth inhibitory effect through more specific cellular mechanisms.

PSSA-α-Toc inhibited the growth of the ER-negative cells MDA-MB-231 by 65% after 6 days of incubation while VES alone by 44%. PSSA alone decreased cell viability by 31%, which is a significantly better effect than on the ER-positive cell line. The effect of the equimolar combination of PSSA with VES inhibited MDA-MB-231 cell growth only by 48%, further suggesting that there is no actual biochemical interaction in the culture media leading to a common cell growth inhibitory effect. Under the current experimental conditions MDA-MB-231 have shown a 31% decrease to comparable concentrations of 5-fluouracil, a known chemotherapeutic agent commonly used against breast cancer. The compounds of formula (I) therefore have cell growth inhibitory properties superior to those of standard chemotherapeutics as well as those of VES at equimolar concentrations.

The invention has been described in detail with particular reference to preferred embodiments thereof, but it will be understood that variations and modifications can be effected within the spirit and scope of the invention.

We claim:

1. Compounds having the formula

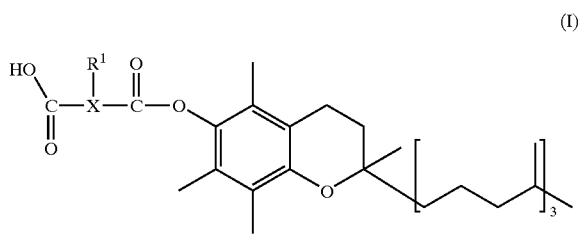

(I)

wherein X is a chain of 2 or 3 carbon atoms joining the 2 carbonyl groups to which they are bonded; and $R^1$ is a group having the formula —Y—$R^4$ wherein Y is a selenium, tellurium or sulfur atom and $R^4$ is an alkyl, cycloalkyl or aryl radical.

2. A compound according to claim 1 wherein Y is selenium or tellurium and $R^4$ is alkyl of 1 to about 6 carbon atoms, phenyl or phenyl substituted with one or two substituents selected from alkyl, alkoxy, nitro, and halogen.

3. A compound according to claim 1 wherein $R^1$ is phenylselenyl.

4. Compounds having the formula

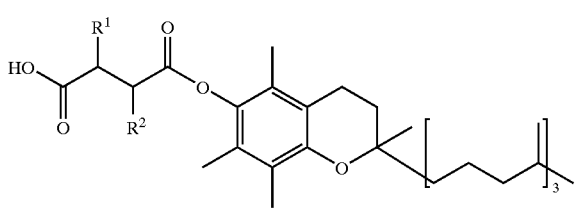

wherein $R^1$ and $R^2$ each is hydrogen or phenylselenyl, provided that $R^1 \neq R^2$.

5. A compound having the formula

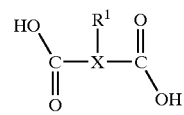

wherein X is a chain of 2 or 3 carbon atoms joining the 2 carbonyl groups to which they are bonded; and $R^1$ is a group having the formula —Y—$R^4$ wherein Y is a selenium, tellurium or sulfur atom and $R^2$ is an alkyl, cycloalkyl or aryl radical.

6. A compound according to claim 5 wherein Y is selenium or tellurium and $R^4$ is alkyl of 1 to about 6 carbon atoms, phenyl or phenyl substituted with one or two substituents selected from alkyl, alkoxy, nitro, and halogen.

7. A compound according to claim 5 which is 2-phenylselenylsuccinic acid.

8. A compound having the formula

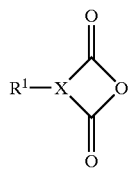

wherein X is a chain of 2 or 3 carbon atoms joining the 2 carbonyl groups to which they are bonded; and $R^1$ is a group having the formula —Y—$R^4$ wherein Y is a selenium, tellurium or sulfur atom and $R^2$ is an alkyl, cycloalkyl or aryl radical.

9. A compound according to claim 8 wherein Y is selenium or tellurium and $R^4$ is alkyl of 1 to about 6 carbon atoms, phenyl or phenyl substituted with one or two substituents selected from alkyl, alkoxy, nitro, and halogen.

10. A compound according to claim 8 which is 2-phenylselenylsuccinic anhydride.

11. A process for the preparation of a compound defined in claim 1 comprising the steps of:

(1) contacting a compound having the formula Z—Y—$R^4$ with a dicarboxylic acid anhydride having the formula:

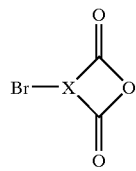

in the presence of an alkanol having the formula $R^3$—OH to obtain an ester having the formula:

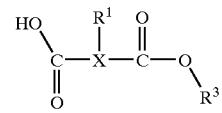

(2) separating the ester of formula (III) produced in step (1) from the alkanol solvent;

(3) contacting the ester of formula (III) with aqueous inorganic acid to convert the ester to the corresponding dicarboxylic acid;

(4) contacting the dicarboxylic acid formed in step (3) with acetic anhydride to convert the dicarboxylic acid to an anhydride having the formula:

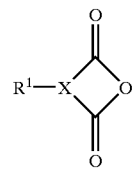

and (5) contacting the anhydride of formula (IV) with RRR-α-tocopherol to obtain an α-tocopherol ester defined in claim 1;

wherein X and $R^1$ are defined in claim 1; $R^3$ is alkyl of 1 to 3 carbon atoms and Z is an alkali metal.

12. A process according to claim 1 wherein X is ethylene and R1 is phenylselanyl.

13. A method for inhibiting the growth of a cancer cell line selected from estrogen-receptor positive MCF-7 and estrogen-receptor negative MDA-MB-231 which comprises contacting the cancer cell line with a compound defined in claim 1.

14. A method according to claim 13 wherein the cancer cell line is contacted with a compound defined in claim 2.

15. A method according to claim 13 wherein the cancer cell line is contacted with a compound defined in claim 4.

* * * * *